US008445195B2

(12) United States Patent
Fernández et al.

(10) Patent No.: US 8,445,195 B2
(45) Date of Patent: May 21, 2013

(54) METHOD AND KIT FOR THE DETECTION OF BACTERIAL SPECIES BY MEANS OF DNA ANALYSIS

(75) Inventors: Pedro Anda Fernández, Madrid (ES); Raquel Escudero Nieto, Madrid (ES); Isabel Jado García, Madrid (ES); Isabel Rodríguez Moreno, Madrid (ES); Maria Isabel Jimenez Alonso, Madrid (ES)

(73) Assignee: Instituto de Salud Carlos III, Madrid (ES)

( * ) Notice: Subject to any disclaimer, the term of this patent is extended or adjusted under 35 U.S.C. 154(b) by 656 days.

(21) Appl. No.: 11/922,063

(22) PCT Filed: Jun. 15, 2006

(86) PCT No.: PCT/ES2006/070082

§ 371 (c)(1),
(2), (4) Date: Jan. 11, 2008

(87) PCT Pub. No.: WO2006/136639

PCT Pub. Date: Dec. 28, 2006

(65) Prior Publication Data

US 2008/0248473 A1 Oct. 9, 2008

Related U.S. Application Data

(60) Provisional application No. 60/691,231, filed on Jun. 17, 2005.

(30) Foreign Application Priority Data

Jun. 17, 2005 (ES) .................................. 200501481

(51) Int. Cl.
*C12Q 1/68* (2006.01)

(52) U.S. Cl.
USPC .......... 435/6.1; 435/6.11; 435/6.12; 435/6.15

(58) Field of Classification Search
None
See application file for complete search history.

(56) References Cited

U.S. PATENT DOCUMENTS 6,300,072 B1 10/2001 Jensen

FOREIGN PATENT DOCUMENTS

| | | | |
|---|---|---|---|
| DE | 19945916 | | 4/2001 |
| EP | 1013775 | A1 | 6/2000 |
| JP | 2004283153 | A | 10/2004 |
| WO | WO 01/23606 | | 4/2001 |
| WO | 02070728 | A2 | 9/2002 |

OTHER PUBLICATIONS

Bekker et al (Veterinary Microbiology, 89, 2002, p. 223-238).*
Christova (Eur J Clin Microbiol Infect Dis (2003) 22: 535-542).*
Coiras, M.T., et al., Oligonucleotide array for simultaneous detection of respiratory viruses using a reverse-line blot hybridization assay. J. Med. Virol. Jun. 2005, vol. 76, pp. 256-264. Publicaddo on line el Apr. 15, 2005.
Bekker, C.P.J., et al., Simultaneous detection of anaplasma and Erluchia species in rumiants and detection of *Erlichia rumiantium* and *Amblyomma variegatum* ticks by reverse line blot hybridization. Vet. Microbiol. Oct. 22, 2002, vol. 89, No. 2-3, pp. 223-228.
Schouls, L.M. et al., Detection and identification of Erlichia, *Borrelia burgorferi* Sensu Lato, and Bartonella species in dutch Ixodes ricinus ticks. J.Clin. Microbiol. Jul. 1999, vol. 37, No. 7, pp. 2215-2222.
Lutz, H ., Sequence No. 42 from EP 1013775 “Quantitative polymerase chain reaction using a fluorogenic real-time detection system”, Jun. 20, 2000.
Vitorino Liliana et al: “rRNA intergenic spacer regions for phylogenetic analysis of *Rickettsia* species.” Annals of the New York Academy of Sciences Jun. 2003 LNKD-PUBMED:12860714, vol. 990, Jun. 2003, pp. 726-733, XP002605093 ISSN: 0077-8923.
Fournier Pierre-Edouard et al: “Use of highly variable intergenic spacer sequences for multi spacer typing of *Rickettsia conorii* strains.” Journal of Clinical Microbiology Dec. 2004 LNKD-PUBMED:15583310, vol. 42, No. 12, Dec. 2004, pp. 5757-5766, XP002605094 ISSN: 0095-1137.
Zhu Yong et al: “Multispacer typing of *Rickettsia prowazekii* enabling epidemiological studies of epidemic typhus.” Sep. 2005, Journal of Clinical Microbiology Sep. 2005 LNKDPUBMED: 16145131, vol. 43, Nr. 9, pp. 4708-4712, XP002605095 ISSN: 0095-1137.
Li Dong-Mei et al: “Study on *Bartonella* infection using molecular biological diagnostic techniques from China” Zhonghua Liu Xing Bing Xue Za Zhi = Zhonghua Liuxingbingxue Zazhi vol. 25, No. 7, Jul. 1, 2004, pp. 602-606, XP009140145.
Roux V et al: “Inter- and Intraspecies Identification of *Bartonella* (*Rochalimaea*) Species” Journal of Clinical Microbiology, American Society for Microbiology, Washington, DC, US, vol. 33, Jun. 1, 1995, pp. 1573-1579, XP002926816 ISSN: 0095-1137.
Maggi Ricardo G et al: “Potential limitations of the 16S-23S rRNA intergenic region for molecular detection of —*Bartonella* species.” Journal of Clinical Microbiology Mar. 2005 LNKD-PUBMED:15750079, vol. 43, No. 3, Mar. 2005, pp. 1171-1176, XP002606098 ISSN: 0095-1137.
Dillon B et al: “Limited diversity among human isolates of *Bartonella henselae*.” Journal of Clinical Microbiology Dec. 2002 LNKD-PUBMED:12454174, vol. 40, No. 12, Dec. 2002, pp. 4691-4699, XP002606099 ISSN: 0095-1137.
Minnick Michael F et al: “Identification of *Bartonella* using PCR: Genus- and species-specific primer sets” Journal of Microbiological Methods, vol. 31, No. 1-2, Dec. 1997, pp. 51-57, XP002606100 ISSN: 0167-7012.
Blaskovic D et al: “Oligo-chip based detection of tick-borne bacteria” FEMS Microbiology Letters, Blackwell Publishing, Amsterdam, NL, vo. 1. 243, No. 2, Feb. 15, 2005, pp. 473-478, XP025393795 ISSN: 0378-1097 [retrieved on Feb. 15, 2005].

(Continued)

*Primary Examiner* — Albert Navarro
(74) *Attorney, Agent, or Firm* — Leason Ellis LLP

(57) ABSTRACT

The present invention relates to the detection and identification of different bacterial species, all of which cause zoonosis, based on DNA analysis. More specifically, the invention provides the primers, probes, genes and genic regions required to apply a method for the simultaneous detection of bacteria and bacterial groups belonging to the genera *Anaplasma, Ehrlichia, Borrelia, Bartonella, Coxiella, Rickettsia* and *Francisella* based on Multiple PCR analysis by RLB (Reverse Line Blotting), in addition to providing a kit to carry out said analysis.

7 Claims, 3 Drawing Sheets

OTHER PUBLICATIONS

Schouls Lmet al: "Detection and identification *Ehrlichia, Borrelia burgdorferi* Sensu Lato, and *Bartonella* species in dutch *Ixodes ricinus* ticks" Journal of Clinical Microbiology, Washington, DC, US, vol. 37, No. 7, Jul. 1, 1999, pp. 2215-2222, XP003005400 ISSN: 0095-1137.

Long Gwet al: "Detection of *Francisella tularensis* in Blood by Polymerase Chain Reaction" Journal of Clinical Microbiology, Washington, DC, US, vol. 31, No. 1, Jan. 1, 1993, pp. 152-154, XP000614920 ISSN: 0095-1137.

Hoover T A et al: "A *Coxiella burnetti* repeated DNA element resembling a bacterial insertion sequence." Journal of Bacteriology Sep. 1992, vol. 174, No. 17, Sep. 1992, pp. 5540-5548, XP002539104 ISSN: 0021-9193.

Klee Silke R et al: "Highly sensitive real-time PCR for specific detection and quantification of *Coxiella burnetii*" BMC Microbiology, Biomed Central, London, GB, vol. 6, No. 1, Jan. 19, 2006, p. 2, XP021002673 ISSN: 1471-2180.

* cited by examiner

METHOD AND KIT FOR THE DETECTION OF BACTERIAL SPECIES BY MEANS OF DNA ANALYSIS

This application is a U.S. national phase application under 35 U.S.C. §371 of International Patent Application No. PCT/ES2006/070082 filed Jun. 15, 2006, which claims the benefit of priority to Spanish Patent Application No. 200501481 filed Jun. 17, 2005 and U.S. Provisional Patent Application No. 60/691,231 filed Jun. 17, 2005, all of which are hereby incorporated by reference in their entireties. The International Application was published in Spanish on Dec. 28, 2006 as WO 2006/136639.

FIELD OF THE INVENTION

The present invention relates to the detection and identification of different bacterial species, all of which cause zoonosis, based on DNA analysis. More specifically, the invention provides a method and kit for the simultaneous detection of bacteria and bacterial groups belonging to the genera *Anaplasma, Ehrlichia, Borrelia, Bartonella, Coxiella, Rickettsia* and *Francisella* based on DNA amplification.

BACKGROUND

To date, about 200 zoonotic diseases (bartonelosis, leptospirosis, Lyme borreliosis, etc.), which affect humans have been described. In third world countries, they represent one of the main causes of death and entail substantial economic loss. Coexistence with animals, lack of sanitary infrastructure and low cultural level continue to be the main allies of these diseases.

Certain types of zoonosis are now thriving in industrialized countries as a consequence of population increases in urban and periurban areas, and increased movement of animals across international borders, which entails the risk of introducing exotic diseases into the environment.

These circumstances, coupled with the frequent findings of arthropods infected by more than one of the pathogens included in the present invention, increase the possibility of more than one of the bacterial species included in the present invention being transmitted in a single sting.

As a result, hospitalizations due to medical profiles produced by human contact with animals or different classes of arthropods, such as mosquitoes, ticks, fleas, lice, mites, etc., which act as vectors or pathogen reservoirs, is becoming increasingly common. Said medical profiles, due to their high degree of similarity, do not allow a fast and reliable identification of the pathogenous agent, so that specific and fast treatment is not possible and is occasionally administered too late. This undoubtedly justifies the need for a comprehensive detection method.

The diagnostic methods currently available are limited to detecting antibodies which, in general, is retrospective and of little use to treating patients in acute-phase states. Culture is not considered a diagnostic method, due both to its technological complexity, which excludes it from regular practice in hospital microbiology laboratories, and to the need for P3 facilities.

Molecular diagnosis by genome amplification by means of PCR represents a diagnostic option of great value. However, clinical samples of sufficient quantity for pathogen testing or the methodology required to carry out different tests are not always available.

A paper has recently been published (Blaskovic D. et al. 2005. Oligo-based detection of tick-borne bacteria. FEMS Microbiology Letters 243:273-8) which describes a method for the detection of 5 out of 6 pathogens proposed by the present invention. Said method is based on ribosomal DNA analysis and uses universal primers, which amplify the genetic material of both target and non-target bacteria, due to which its sensitivity is substantially reduced.

Other methods, such as those described by U.S. Pat. Nos. 6,300,072 and 6,518,020, are capable of detecting and identifying bacteria of the genus *Bartonella*, by using the same DNA region (intergenic space 16S-23S). However, the number of species within this genus has increased substantially since said patents were filed and their approximation, which consists of discriminating between species according to the size of the amplicon obtained during PCR, is not useful for certain known species within the same genus which are similar in size to the amplified fragment.

While the method provided by the present invention also proposes using intergenic region 16S-23S for the detection of species belonging to the genus *Bartonella*, improvements have been introduced with respect to the previously described procedures, as it is capable of detecting a much wider range of species within the same and other genera, using completely new probes and primers with maximum sensitivity levels.

For the detection of *Coxiella burnetii*, the present invention uses the same primers and DNA region (insertion sequence IS1111) as the previously described methods. Said detection has been improved by combining it with another series of completely new tests aimed at identifying other bacterial species, which can be transmitted by the same vectors and also provide a new hybridization probe for the detection of *Coxiella burnetii.*

DETAILED DESCRIPTION

Definitions: Multiple PCR or Multiplex PCR: PCR (Polymerase Chain Reaction) is a system whereby the number of copies of a specific nucleotide sequence of an organism is amplified or increased using two primers. Multiple PCR or Multiplex PCR is a variation of PCR which allows the simultaneous amplification of more than one target sequence using more than one pair of primers.

The present invention solves the problem of the tediousness and complexity of detecting a high number of bacteria that cause zoonosis which can be clinically and/or epidemiologically indistinguishable, through the development of a method and Kit for the simultaneous detection of bacterial species that cause zoonosis belonging to the genera: *Anaplasma, Ehrlichia, Borrelia, Bartonella, Coxiella, Rickettsia* and *Francisella.*

The solution found by the present invention includes simultaneously analyzing different bacterial DNA regions to determine which species are present in both cases. Specifically, the 16S rRNA gene is analyzed in order to detect the presence of *Anaplasma, Ehrlichia* and *Borrelia*; intergenic space 23S-5S rRNA is analyzed to detect the presence of *Rickettsia*; the gene which codes for the precursor of the main membrane protein TUL4 is analyzed to detect the presence of *Francisella*; the transposase IS1111 gene is analyzed to detect the presence of *Coxiella* and intergenic space 16S-23S is analyzed to detect the presence of *Bartonella.*

According to the above, a first aspect of the invention relates to a method for the sample-based detection of bacteria, comprised of the following steps:

i) Placing the sample under analysis in contact with a reaction mixture containing specific primers to carry out Multiplex PCR.

ii) Amplifying by means of polymerase chain reaction.

iii) Identifying the formation of the products in the previous step, said information being indicative of the presence or absence of zoonosis-causing bacteria.

In relation to this first aspect of the invention, said invention provides a method to simultaneously detect:

*Anaplasma phagocytophilum, A. bovis, A. equi, A. marginale, A. centrale* and *A. ovis.*

*Ehrlichia chaffeensis* and *E. Ewingii.*

*Bartonella henselae, B. quintana, B. clarridgeiae, B. elizabethae, B. grahamii, B. vinsonii* subspecies *berkhofii, B. vinsonii* subspecies *vinsonii, B. vinsonii* subspecies *aurupensis, B. bacilliformis, B. alsatica, B. bovis, B. doshiae, B. koehlerae, B. schoen-buchensis, B. taylori and B. tribocorum.*

All of the species belonging to the genus *Borrelia.*

*Coxiella burnetii.*

Any subspecies of *Francisella turalensis*, including *F tularensis* subsp. *tularensis, F. tularensis* subsp. *holarctica* and *F. tularensis* subsp. *novicida* which are jointly detected, and variant 3523 of the same species and so-called endosymbionts of different species of ixodides and argasides, which are detected differentially.

The genus *Rickettsia*, and group that causes spotted fever and the group that causes typhus, the species *Rickettsia akari, R. bellii, R. slovaca, R. conorii, R. aeschlimannii, R. ricketsii, R. sibirica, R. helvetica, R. felis, R. australis, R. prowazekii and R. typhy* (*R. mooserii*).

all of which are capable of causing zoonosis, jointly infecting an individual and being difficult to identify by simple observation of medical profiles, based on the amplification and analysis of the genes or specific genic regions presented in Tables 1-6.

According to a specific embodiment of this first aspect of the invention, DNA fragments included or comprised within the sequences, the access numbers of which are shown in Tables 1-6 below, are amplified.

According to a more specific embodiment of this first aspect of the invention, the amplified regions have a size of between 99 and 686 nucleotides and contain variable regions used for identification. According to an even more specific embodiment of the invention, the variable regions contain or are included within sequences SEQ ID NO:55 to SEQ ID NO:93 or complementary sequences, the positions of which are shown in Tables 1 to 6.

According to another embodiment of this first aspect of the invention, the amplification products that allow different bacterial species and groups to be identified are detected by means of probes. According to a more preferred embodiment, said probes have a length of between 15 and 25 nucleotides. And, according to an even more preferred embodiment, the probes have sequences which comprise or are included within sequences SEQ ID NO:3-6; SEQ ID NO:9-24; SEQ ID NO:27; SEQ ID NO:30; SEQ ID NO:33-35; SEQ ID NO:38-51; or complementary sequences (Tables 1-6).

The primers can be designed by means of multiple alignment using computer programs such as CLUSTAL X, which allows the identification of highly conserved regions that act as moulds. According to another specific embodiment of this first aspect of the invention, the primers hybridize the genes indicated in Tables 1 to 6 below and particularly those with sequences with the access numbers shown in Tables 1-6 below. According to an even more specific embodiment, the primers have sequences which comprise or are included within SEQ ID NO:1-2; SEQ ID NO:7-8; SEQ ID NO:25-26; SEQ ID NO:28-29; SEQ ID NO:31-32; SEQ ID NO:36-37; or complementary sequences.

Brief explanation of the Tables:

Column 1 (organism) indicates the bacterial species or group of bacterial species detected in each case.

Column 2 (gene) indicates the gene or genome region used to detect the bacterial species or group of species in column 1.

Column 3 (primer) indicates the sequence of the pair of primers required to carry out the amplification of variable gene regions or genome regions indicated in each Table (column 2).

Column 4 (probe) indicates the sequence of the probes used to detect the bacterial species or group of species referenced in column 1 of each Table.

Column 5 (sequence 5'-3') indicates the sequence references of the variable regions which are amplified to detect each bacterial species or group of species.

Column 6 (position 5'-3'):

The first row: indicates a sequence code relative to a gene or genome region referenced in column 2, in addition to the specific position of said sequence in which the primer is hybridized (column 3).

The second to the last row of each Table indicate a sequence code relative to a gene or genome region referenced in column 2, in addition to the specific position of said sequence to which the probe is joined (column 4).

TABLE 1

*Anaplasma* and *Ehrlichia*: sequence of each of the primers and probes used in the process and their relative position within gene 16S rRNA.

| ORGANISM | GENE | PRIMER | PROBES | SEQUENCE 5'-3' | POSITION 5'-3' |
|---|---|---|---|---|---|
| *Anaplasma* spp<br>*Ehrlichia* spp | 16S | SEQ ID 1<br>(16S/AE-F)<br>SEQ ID 2<br>(16S/AE-R) | | | 9-30<br>(U02521)<br>109-86<br>(U02521) |
| *Anaplasma phagocytophilum*<br>*A. bovis*<br>*A. equi* | 16S | SEQ ID 1<br>(16S/AE-F)<br>SEQ ID 2<br>(16S/AE-R) | SEQ ID 3<br>(S-PHA) | SEQ ID 57 | 52-73<br>(U02521)<br>8-29<br>(AF470698)<br>8-29<br>(AF172167) |
| *Ehrlichia chaffeensis* | 16S | SEQ ID 1<br>(16S/AE-F)<br>SEQ ID 2<br>(16S/AE-R) | SEQ ID 4<br>(S-CHA) | SEQ ID 58 | 51-71<br>(AF147752) |

TABLE 1-continued

*Anaplasma* and *Ehrlichia*: sequence of each of the primers and probes used in the process and their relative position within gene 16S rRNA.

| ORGANISM | GENE | PRIMER | PROBES | SEQUENCE 5'-3' | POSITION 5'-3' |
|---|---|---|---|---|---|
| *E. ewingii* | 16S | SEQ ID 1 (16S/AE-F) SEQ ID 2 (16S/AE-R) | SEQ ID 5 (S-EWI) | SEQ ID 59 | 46-66 (U96436) |
| *A. marginale* *A. centrale* *A. ovis* | 16S | SEQ ID 1 (16S/AE-F) SEQ ID 2 (16S/AE-R) | SEQ ID NO 6 (S-MCO) | SEQ ID 60 | 53-71 (AJ633048) 72-90 (AF414869) 72-90 (AF414870) |

TABLE 2

*Bartonella*: sequence of each of the primers and probes used in the process and their relative position within intergenic space 16S-23S rRNA.

| ORGANISM | GENE | PRIMER | PROBES | SEQUENCE 5'-3' | POSITION 5'-3' |
|---|---|---|---|---|---|
| *Bartonella* spp. | 16S-23S | SEQ ID 7 (BAR/16-23F) SEQ ID 8 (BAR/16-23R) | | | 494-515 (AF369527) 908-889 (AF369527) |
| *B. henselae* | 16S-23S | SEQ ID 7 (BAR/16-23F) SEQ ID 8 (BAR/16-23R) | SEQ ID 9 (S-HENS) | SEQ ID 61 | 793-814 (AF369527) |
| *B. quintana* | 16S-23S | SEQ ID 7 (BAR/16-23F) SEQ ID 8 (BAR/16-23R | SEQ ID 10 (S-QUIN) | SEQ ID 62 | 622-641 (AF368396) |
| *B. clarridgeiae* | 16S-23S | SEQ ID 7 (BAR/16-23F) SEQ ID 8 (BAR/16-23R | SEQ ID 11 (S-CLAR) | SEQ ID 63 | 512-531 (AF312497) |
| *B. elizabethae* | 16S-23S | SEQ ID 7 (BAR/16-23F) SEQ ID 8 (BAR/16-23R | SEQ ID 12 (S-ELIZ) | SEQ ID 64 | 807-827 (L35103) |
| *B. grahamii* | 16S-23S | SEQ ID 7 (BAR/16-23F) SEQ ID 8 (BAR/16-23R | SEQ ID 13 (S-GRAH2) | SEQ ID 65 | 491-514 (AJ269790) |
| *B. vinsonii berkhofii* | 16S-23S | SEQ ID 7 (BAR/16-23F) SEQ ID 8 (BAR/16-23R | SEQ ID 14 (S-VIN-B) | SEQ ID 66 | 2242-2261 (AF143446) |
| *B. vinsonii arupensis* | 16S-23S | SEQ ID 7 (BAR/16-23F) SEQ ID 8 (BAR/16-23R | SEQ ID 15 (S-VIN-A1) | SEQ ID 67 | 686-706 (AF442952) |
| *B. vinsonii vinsonii* | 16S-23S | SEQ ID 7 (BAR/16-23F) SEQ ID 8 (BAR/16-23R | SEQ ID 16 (S-VIN-A2) | SEQ ID 68 | 821-841 (AF312504) |
| *B. bacilliformis* | 16S-23S | SEQ ID 7 (BAR/16-23F) SEQ ID 8 (BAR/16-23R | SEQ ID 17 (S-BACI) | SEQ ID 69 | 474-493 (AJ422181) |
| *B. alsatica* | 16S-23S | SEQ ID 7 (BAR/16-23F) SEQ ID 8 (BAR/16-23R | SEQ ID 18 (S-ALS) | SEQ ID 70 | 589-608 (AF312506) |
| *B. bovis* | 16S-23S | SEQ ID 7 (BAR/16-23F) SEQ ID 8 (BAR/16-23R | SEQ ID 19 (S-BOV2) | SEQ ID 71 | 455-478 (AY116638) |
| *B. doshiae* | 16S-23S | SEQ ID 7 (BAR/16-23F) SEQ ID 8 (BAR/16-23R | SEQ ID 20 (S-DOSH) | SEQ ID 72 | 724-743 (AJ269786) |

TABLE 2-continued

*Bartonella*: sequence of each of the primers and probes used in the process and their relative position within intergenic space 16S-23S rRNA.

| ORGANISM | GENE | PRIMER | PROBES | SEQUENCE 5'-3' | POSITION 5'-3' |
|---|---|---|---|---|---|
| *B. koehlerae* | 16S-23S | SEQ ID 7 (BAR/16-23F) SEQ ID 8 (BAR/16-23R | SEQ ID 21 (S-KOE) | SEQ ID 73 | 778-803 (AF312490) |
| *B. schoenbuchensis* | 16S-23S | SEQ ID 7 (BAR/16-23F) SEQ ID 8 (BAR/16-23R | SEQ ID 22 (S-SCHO2) | SEQ ID 74 | 446-466 (AY116639) |
| *B. taylori* | 16S-23S | SEQ ID 7 (BAR/16-23F) SEQ ID 8 (BAR/16-23R | SEQ ID 23 (S-TAY) | SEQ ID 75 | 655-673 (AJ269784) |
| *B. tribocorum* | 16S-23S | SEQ ID 7 (BAR/16-23F) SEQ ID 8 (BAR/16-23R | SEQ ID 24 (S-TRIB) | SEQ ID 76 | 692-713 (AF312505) |

TABLE 3

*Borrelia*: sequence of each of the primers and probes used in the process and their relative position within gene 16S rRNA.

| ORGANISM | GENE | PRIMER | PROBES | SEQUENCE 5'-3' | POSITION 5'-3' |
|---|---|---|---|---|---|
| *Borrelia* spp. | 16S | SEQ ID 25 (BOF-3) SEQ ID 26 (BOR) | | | 336-356 (AJ224139) 567-547 (AJ224139) |
| *Borrelia* | 16S | SEQ ID 25 (BOF-3) SEQ ID 26 (BOR) | SEQ ID 27 (SG-BOR3) | SEQ ID 77 | 364-383 (AJ224139) |

TABLE 4

*Coxiella*: sequence of each of the primers and probes used in the process and their relative position within insertion sequence (transposase) IS1111.

| ORGANISM | GENE | PRIMER | PROBES | SEQUENCE 5'-3' | POSITION 5'-3' |
|---|---|---|---|---|---|
| *Coxiella burnetii* | Transposase IS1111 | SEQ ID 28 (TRANS 1) SEQ ID 29 (TRANS 2) | | | 200-221 (M80806) 885-865 (M80806) |
| *Coxiella burnetii* | Transposase IS1111 | SEQ ID 28 (TRANS 1) SEQ ID 29 (TRANS 2) | SEQ ID 30 (S-IS1111) | SEQ ID 78 | 520-539 (M80806) |

TABLE 5

*Francisella*: Amplified gene, sequence of each of the primers and probes used in the process and their relative position.

| ORGANISM | GENE | PRIMER | PROBES | SEQUENCE 5'-3' | POSITION 5'-3' |
|---|---|---|---|---|---|
| *Francisella* spp. | 17 kDa Tul4 | SEQ ID 31 (FT594) SEQ ID 32 (FT827) | | | 593-617 (M32059) 825-804 (M32059) |
| *F. tularensis* | 17 kDa Tul4 | SEQ ID 31 (FT594) SEQ ID 32 FT827 | SEQ ID 33 (S-TUL) | SEQ ID 79 | 658-680 (M32059) |
| Variant 3523 | 17 kDa Tul4 | SEQ ID 31 (FT594) SEQ ID 32 FT827 | SEQ ID 34 (S-TUL3523) | SEQ ID 80 | 169-188 (AY243029) |

TABLE 5-continued

*Francisella*: Amplified gene, sequence of each of the primers and probes used in the process and their relative position.

| ORGANISM | GENE | PRIMER | PROBES | SEQUENCE 5'-3' | POSITION 5'-3' |
|---|---|---|---|---|---|
| Endosymbionts | 17 kDa Tul4 | SEQ ID 31 (FT594) SEQ ID 32 (FT827) | SEQ ID 35 (S-ENDOS2) | SEQ ID 81 | 533-553 (AY375423) |

TABLE 6

*Rickettsia*: sequence of each of the primers and probes used in the process and their relative position within genes 238, 58 rRNA and within intergenic space 23S-5S rRNA.

| ORGANISM | GENE | PRIMER | PROBES | SEQUENCE 5'-3' | POSITION 5'-3' |
|---|---|---|---|---|---|
| *Rickettsia* spp. | 23S-5S | SEQ ID 36 (RCK/23-5-F) SEQ ID 37 (RCK/23-5-R) | | | 1-22 (AY125012) 388-367 (AY125012) |
| Generic | 23S-5S | SEQ ID 36 (RCK/23-5-F) SEQ ID 37 (RCK/23-5-R) | SEQ ID 38 (SG-RICK) | SEQ ID 82 | 51-71 (AY125012) |
| Spotted Fever Group | 23S-5S | SEQ ID 36 (RCK/23-5-F) SEQ ID 37 (RCK/23-5-R) | SEQ ID 39 (SG-SFG) | SEQ ID 83 | 123-141 (AY125012) |
| *R. akari* | 23S-5S | SEQ ID 36 (RCK/23-5-F) SEQ ID 37 (RCK/23-5-R) | SEQ ID 40 (S-AKA4) | SEQ ID 84 | 291.105-291.126 (AAFE01000001) |
| *R. bellii* | 23S-5S | SEQ ID 36 (RCK/23-5-F) SEQ ID 37 (RCK/23-5-R) | SEQ ID 41 (S-BELLII) | SEQ ID 85 | 2721-2743 (U11015) |
| *R. slovaca* | 23S-5S | SEQ ID 36 (RCK/23-5-F) SEQ ID 37 (RCK/23-5-R) | SEQ ID 42 (S-SLO) | SEQ ID 86 | 194-211 (AY125009) |
| *R. conorii* | 23S-5S | SEQ ID 36 (RCK/23-5-F) SEQ ID 37 (RCK/23-5-R) | SEQ ID 43 (S-CON) | SEQ ID 87 | 186-204 (AY125012) |
| *R. aeschlimannii* | 23S-5S | SEQ ID 36 (RCK/23-5-F) SEQ ID 37 (RCK/23-5-R) | SEQ ID 44 (S-AESCH) | SEQ ID 88 | 183-204 (AY125016) |
| *R. rickettsii* *R. sibirica* | 23S-5S | SEQ ID 36 (RCK/23-5-F) SEQ ID 37 (RCK/23-5-R) | SEQ ID 45 (S-RI/SI) | SEQ ID 89 | 2814-2833 (U11022) |
| *R. helvetica* | 23S-5S | SEQ ID 36 (RCK/23-5-F) SEQ ID 37 (RCK/23-5-R) | SEQ ID 46 (S-HELV) | SEQ ID 90 | 360-342 (AY125017) |
| *R. felis* | 23S-5S | SEQ ID 36 (RCK/23-5-F) SEQ ID 37 (RCK/23-5-R) | SEQ ID 47 (S-FEL) | SEQ ID 55 | 186-207 (SEQ ID 55) |
| *R. australis* | 23S-5S | SEQ ID 36 (RCK/23-5-F) SEQ ID 37 (RCK/23-5-R) | SEQ ID 48 (S-AUS) | SEQ ID 56 | 230-249 |
| Grupo Tifus | 23S-5S | SEQ ID 36 (RCK/23-5-F) SEQ ID 37 (RCK/23-5-R) | SEQ ID 49 (SG-TG) | SEQ ID 91 | 2804-2827 (U11018) |
| *R. prowazekii* | 23S-5S | SEQ ID 36 (RCK/23-5-F) SEQ ID 37 (RCK/23-5-R) | SEQ ID 50 (S-PROW) | SEQ ID 92 | 2824-2846 (U11018) |

TABLE 6-continued

*Rickettsia*: sequence of each of the primers and probes used in the process and their relative position within genes 238, 58 rRNA and within intergenic space 23S-5S rRNA.

| ORGANISM | GENE | PRIMER | PROBES | SEQUENCE 5'-3' | POSITION 5'-3' |
|---|---|---|---|---|---|
| *R. typhi* (*R. mooserii*) | 23S-5S | SEQ ID 36 (RCK/23-5-F) SEQ ID 37 (RCK/23-5-R) | SEQ ID 51 (S-TYPHI) | SEQ ID 93 | 188-211 (AY125019) |

Given the abundance of PCR inhibitors, such as humic and fulvic acid, heavy metals, heparin, etc. which can produce false negatives and, despite the methods that exist to reduce the concentration of this type of molecules, we recommend (cf. J. Hoorfar et al., "Making internal Amplification control mandatory for diagnostic PCR" J. of Clinical Microbiology, December 2003, pp. 5835) that the PCR tests contain an Internal Amplification Control (IAC). Said IAC is no more than a DNA fragment which is amplified simultaneously with the target sample, in such a way that its absence at the end of the testing process indicates the presence of factors which have caused unwanted development of the PCR.

A second aspect of the invention relates to a method similar to that described in the first aspect of said invention, including at least one IAC, preferably comprised of a DNA sequence of the Tetrahydrocannabinol Synthase gene of the *Cannabis sativa* species and, more preferably, of a sequence with access number AB183705.

According to a more preferred embodiment, a region of the AB183705 sequence is amplified, said sequence being included within SEQ ID NO:94 or complementary sequences (Table 7).

According to another preferred embodiment, the region is amplified by means of specific primers, the sequences of which comprise or are included within SEQ ID NO:52 and SEQ ID NO:53 or complementary sequences.

The method provided by the present invention allows for the detection of the aforementioned bacteria and bacterial groups, independent of sample origin. Said samples may be obtained from biopsies, scrapings, insects, biological fluids (blood, urine, saliva, etc.), field, etc. Once taken, the sample is pretreated in order to carry out Multiple PCR and subsequent amplicon identification.

The invention also provides diagnosis kits to apply the method described by the invention, which contain:

Specific primers with sequences: SEQ ID 1-2, SEQ ID 7-8, SEQ ID 25-26, SEQ ID 28-29, SEQ ID 31-32, SEQ ID 36-37 and optionally SEQ ID 52 y 53 as IAC.

Probes with sequences: SEQ ID 3-6, SEQ ID 9-24, SEQ ID 27, SEQ ID 30, SEQ ID 33-35, SEQ ID 38-51 and optionally SEQ ID 54 (S-CI2) as IAC.

In the same way, said kits can include all the reactive agents required to apply any of the methods described. This includes, without any type of limitation, the use of buffers, polymerases, cofactors to optimize their activity, contamination-preventing agents, etc. On the other hand, the kits can include all of the supports and containers required for their startup and optimization.

The advantages of the present method and the kits with which to apply it include: speed (39 species and bacterial groups can be detected in less than 8 hours), specificity (the initiators used are specific to each species or bacterial group) and a high level of sensitivity.

TABLE 7

Internal control: Amplified gene, sequence of each of the primers and probes used in the process and their relative position.

| ORGANISM | GENE | PRIMER | PROBES | SEQUENCE 5'-3' | POSITION 5'-3' |
|---|---|---|---|---|---|
| IAC (*Cannabis sativa*) | THC Synthase | SEQ ID 52 (CI-F) SEQ ID 53 (CI-R) | | | 77-99 (AB183705) 447-427 (AB183705) |
| *Cannabis sativa* | THC Synthase | SEQ ID 52 (CI-F) SEQ ID 53 (CI-R) | SEQ ID 54 (S-CI2) | SEQ ID 94 | 281-302 (AB183705) |

Within the context of this description, the term "specific" implies that the primers comprise a nucleotide sequence fully complementary to the genes or genic fragments used by the present invention.

The term "variable regions" refers to DNA sequences which allow for the identification of the bacterial species and groups identified by the present invention.

According to another embodiment of the second aspect of the invention, IAC amplification is detected by means of hybridization with probes. According to a more preferred embodiment, said probes have a length of 15 to 25 nucleotides. And, in an even more preferred embodiment, said probes have a sequence comprised or included in SEQ ID NO:54 or complementary sequences.

Within the context of the specification description and claims, the word "comprises" and its variations, such as "comprising", does not intend to exclude other additives, components, constituent elements or stages. Both the examples and complementary drawings do not intend to limit the invention, but should rather be considered an aid to better understand it.

BRIEF DESCRIPTION OF THE DRAWINGS

FIG. 1. Hybridization membrane showing the validation of primers, probes, and variable regions for the detection of

*Anaplasma* and *Ehrlichia* (A), *Borrelia* (B), *Francisella* (C), *Bartonella* (D) and *Coxiella* (E) species, by means of specific probes (Tables 1-5). The S-Cl2 probe refers to the IAC probe (Table 7).

Figure 2:
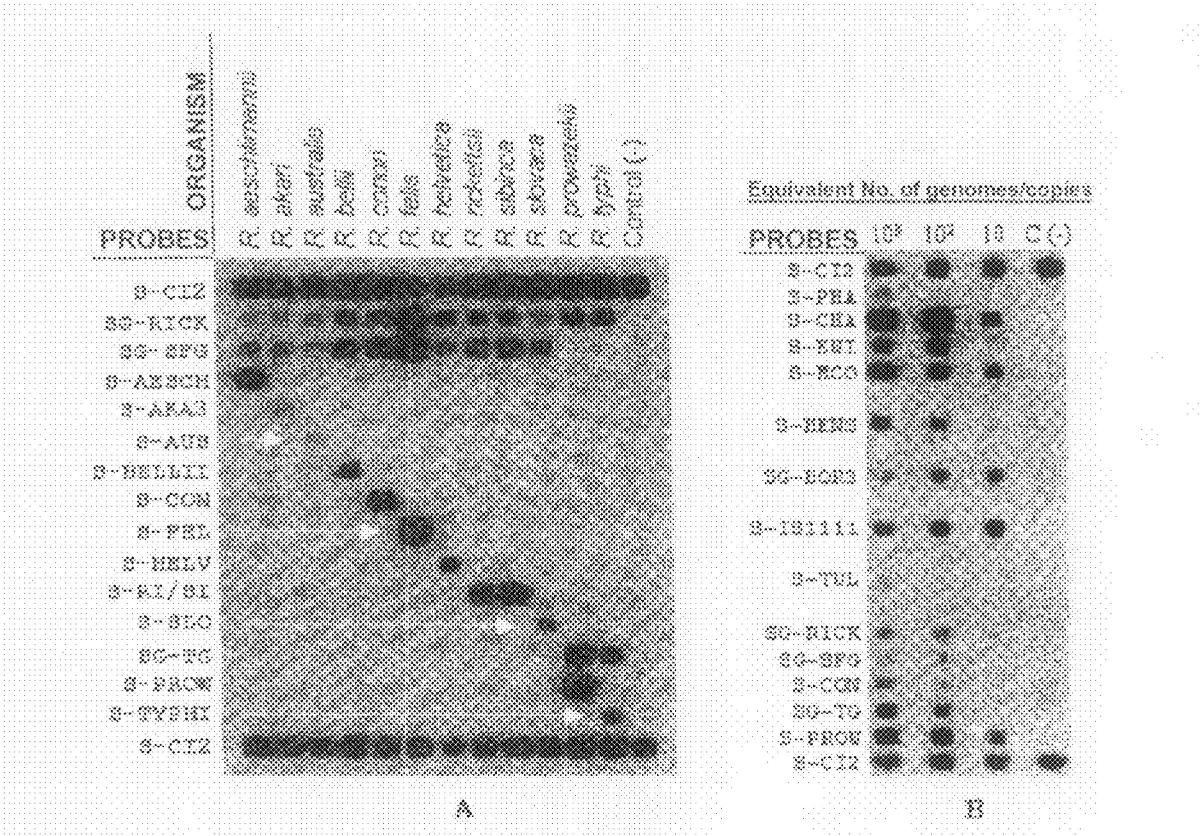

FIG. 2. A) Hybridization membrane showing the validation of primers, probes and variable regions for the detection of *Rickettsia* species; B) Hybridization membrane showing an example of simultaneous detection of species belonging to the 7 genera. In this example: *A. phagocytophilum, A. marginale. E. chaffeensis, E. ewingi, B. henselae, B. burgdorferi, F. tularensis tularensis, R. conorii* and *R. prowazekii*, tested at $10^3$, $10^2$ and 10 equivalent genome/copies. In both cases (A and B) the S-Cl2 probe, which refers to the IAC probe (Table 7), is used.

Figure 3:
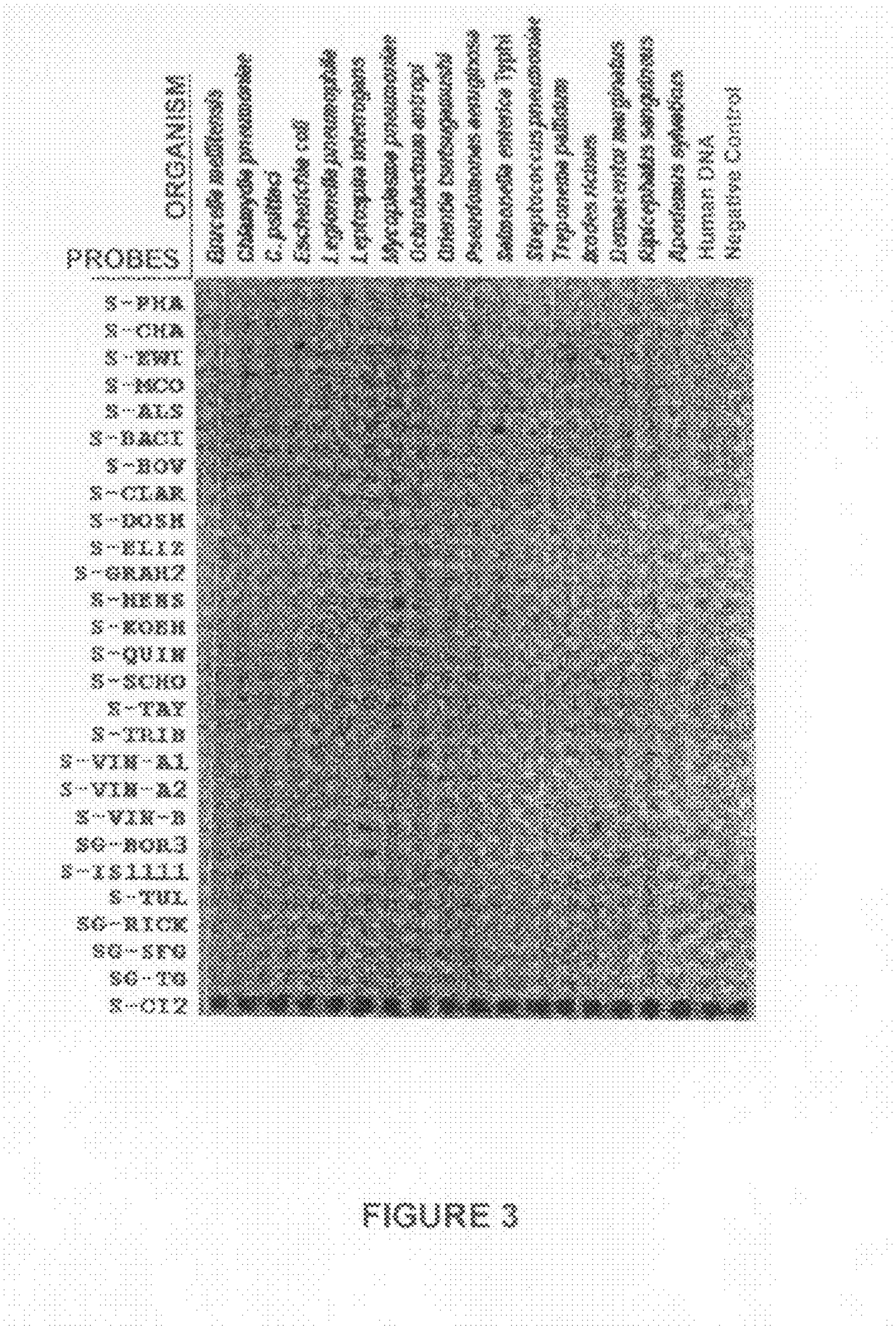

FIG. 3. Hybridization membrane showing the results of a specificity study carried out within the indicated group of probes (Tables 1-7) on different species of bacteria, arthropods and mammals. The results reveal that the probes are not joined to the samples of the organisms tested in any case. The S-Cl2 probe refers to the IAC probe (Table 7).

EXAMPLE

The present invention is next described by reference to an example. The use of this and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the claims, along with the full scope of equivalents to which the claims are entitled.

Alignments, Primer, and Probe Designs

Conserved regions were identified by comparing and aligning multiple sequences obtained from public databases such as Genbank, based on which specific primers were designed (Table 1-6) for use in Multiple PCR. The compatibility between primers, in addition to their optimal concentration, was empirically tested in the same manner as the magnesium salts and bovine serum albumin.

Variable regions were identified based on the selected sequence alignments, which allowed probes to be designed for the differentiation of bacterial species and genic groups (Tables 1-6) through RLB (Reverse Line Blotting) (Kaufhold A, Podbielski A, Baumgarten G, Blokpoel M, Top J, Schouls L. Rapad Typing of group-a streptococci by the use of DNA amplification and nonradioactive allele-specific oligonucleotide probes. FEMS Microbiology Letters 119: 19-25 (1994)).

A first specificity analysis of each of the probes was carried out by comparing its sequence against public databases (Genbank) using computer programs such as BLAST. Specificity was subsequently demonstrated by carrying out tests on a variety of DNA samples of different bacterial and eukaryotic species (FIG. 3).

DNA Culture Mediums and Isolation

The species and genic groups selected for identification were obtained from private collections: the Spanish Type Culture Collection (CECT) and/or sample bank available at the National Microbiology Center (CNM). All of the species analyzed are shown in Table 8.

The isolation of genetic material was carried out using well-known procedures within the art and available on the market (DNA Mini Kit, Qiagen, N. Reference: 51304).

TABLE 8

Origin of DNA used in the invention

| ORGANISM | NATIVE DNA (origin) | SYNTHETIC DNA * |
|---|---|---|
| *Anaplasma phagocytophilum* | X (1) | |
| *A. marginale* | X (1) | |
| *Ehrlichia chaffeensis* | | X |
| *E. ewingii* | | X |
| *Borrelia burgdorferi* | X (2) | |
| *B. garinii* | X (2) | |
| *B. afzelii* | X (2) | |
| *B. lusitaniae* | X (2) | |
| *B. japónica* | X (2) | |
| *B. hermsii* | X (2) | |
| *B. parkeri* | X (2) | |
| *Francisella tularensis tularensis* | X (3) | |
| *F. tularensis* subesp. *holarctica* | X (3) | |
| *F. tularensis* subesp. *Novicida* | X (3) | |
| *Francisella* variant 3523 | | X |
| *Francisella* Endosimbiontes | | X |
| *Bartonella alsatica* | X (4) | |
| *B. bacilliformis* | X (4) | |
| *B. bovis* | X (4) | |
| *B. clarridgeiae* | X (4) | |
| *B. doshiae* | X (4) | |
| *B. elizabethae* | X (4) | |
| *B. grahamii* | X (4) | |
| *B. henselae* | X (4) | |
| *B. koehlerae* | X (4) | |
| *B. quintana* | X (4) | |
| *B. schoenbuchensis* | X (4) | |
| *B. taylorii* | X (4) | |
| *B. tribocorum* | X (4) | |
| *B. vinsonii* subesp. *Arupensis* | X (4) | |
| *B. vinsonii* subesp. *Berkhofii* | X (4) | |
| *B. vinsonii* subesp. *Vinsonii* | X (4) | |
| *Coxiella burnetii* | X (5) | |
| *Rickettsia aeschlimannii* | | X |
| *R. akari* | X (5) | |
| *R. australis* | X (5) | |
| *R. bellii* | X (5) | |
| *R. conori* | X (5) | |
| *R. felis* | X (5) | |
| *R. Helvetica* | X (5) | |
| *R. rickettsii* | X (5) | |
| *R. sibirica* | | X |
| *R. slovaca* | X (5) | |
| *R. prowazekii* | | X |
| *R. typhi* | X (5) | |
| *Brucella melitensis* | X (6) | |
| *Chlamydia pneumoniae* | X (7) | |
| *C. psittaci* | X (7) | |
| *Escherichia coli* | X (6) | |
| *Legionella pneumophila* | X (8) | |
| *Leptospira interrogans* | X (4) | |
| *Micoplasma pneumoniae* | X (7) | |
| *Ochrobactrum antropi* | X (4) | |
| *Orientia tsutsugamushi* | X (5) | |
| *Pseudomonas aeruginosa* | X (4) | |
| *Salmonella enterica* Typhi | X (4) | |
| *Streptococcus pneumoniae* | X (6) | |
| *Treponema pallidum* | X (7) | |
| *Ixodes ricinus* | X (9) | |
| *Dermacentor marginatus* | X (9) | |
| *Rhipicephalus sanguineus* | X (9) | |

TABLE 8-continued

| Origin of DNA used in the invention | | |
|---|---|---|
| ORGANISM | NATIVE DNA (origin) | SYNTHETIC DNA * |
| *Apodemus sylvaticus* | X (9) | |
| Human DNA | X (10) | |
| Internal Control | | X |

Origin of Native DNA:
(1): Positive sample.
(2): Axenic culture medium, as described in: Benach J L, Coleman J L, and Golightly M G. 1988. A murine monoclonal antibody binds an antigenic determinant in outer surface protein A, an immunodominant basic protein of the Lyme disease spirochete. J. Immunol. 140: 265-72.
(3): Axenic culture medium, as described in: Anda P, Segura del Pozo J, Diaz Garcia J M, Escudero R, Garcia Peña F J, Lopez Velasco M C, Sellek R E, Jimenez Chillaron M R, Sanchez Serrano L P, Martinez Navarro J F. 2001. Waterborne outbreak of tularemia associated with crayfish fishing. Emerg. Infect. Dis. 7 (Suppl): 575-82.
(4): Composition of axenic culture mediums specific to each species available at: Jacomo et al. (2002) *Clinical and Diagnostic Laboratory Immunology*, 9 (1) 8-18.
(5): Propagation in cellular cultures using the "shell vial" technique, as described in: Marrero M, Raoult D. 1989. Centrifugation-shell vial technique for rapid detection of Mediterranean spotted fever *rickettsia* in blood culture. Am. J. Trop. Med. Hyg. 40: 197-9.
(6): "Mueller Hinton" agar culture enriched with 5% of ram blood.
(7): DNA extracted from slides for indirect commercial immunofluorescence.
(8): Axenic culture medium, as described in: Edelstein P H. 1981. Improved semiselective medium for isolation of *Legionella pneumophila* from contaminated clinical and environmental samples. J. Clin. Microbiol. 14: 298-303.
(9): DNA extracted from pathogen-free specimens.
(10): DNA extracted from clinical samples of patients with unrelated diseases.

Synthetic DNA

Synthetic DNA was prepared according to the corresponding sequences listed in Tables 1 to 7 (Column 6), by means of consecutive elongation of the DNA chain by PCR, using primers with approximately 70 nucleotides, of which approximately 20 nucleotides interoverlapped.

Amplification, Hybridization and Validation

This step included the experimental analysis of the variable regions detected earlier using PCR for their validation. The isolated DNA was amplified using PCR (Saiki et al., (1985) Science 230, 1350; 1354), applying the following temperature cycle table and reaction mixture composition, together with the specific primers used previously for said purpose.

| Temperature Cycles | | |
|---|---|---|
| Temperature (° C.) | Time | Cycles |
| 94 | 9' | 1 |
| 94 | 15" | |
| 60 | 1' | 40 |
| 65 | 4' | |
| 65 | 7' | 1 |

Reaction mixture composition for a final volume of 50 μL:

| | |
|---|---|
| $H_2O$: | According to final DNA volume |
| Buffer Taq Gold LD: | 9 μL |
| $Cl_2Mg$ [3 mM]: | 6 μL |
| dNTPs [200 mM]: | 1 μL × 4 |
| BSA [0.8 ug/uL]: | 4 μL |
| 14 specific Primers (SEQ ID 1-2, SEQ ID 7-8, SEQ ID 25-26, SEQ ID 28-29, SEQ ID 31-32, SEQ ID 36-37, SEQ ID 52-53) [50 pm/μL]: | 0.5 μL of each (7 μL) |
| Taq Gold LD: | 0.5 μL [2.5 units] |
| Problem DNA: | maximum 800 ng |

The amplicons were sequenced for their validation, verifying that the amplified sequence coincided with the variable sequences inferred from bioinformatic studies. Subsequently, the amplicons were hybridized with specific probes according to the RLB protocol described by Sjoerd G. T. Rijpkema et al., Journal of Clinical Microbiology, December 1995, p. 3091-3095, although applying the following modifications (FIGS. 1 and 2A):

| | |
|---|---|
| Substrate: | Super Signal West Dura (Pierce, Ref: 34075) |
| Probes: | used with a concentration of between 0.2 and 3.2 picomoles/microliter |
| Incubation: | at 55° C. |
| Wash: | at 52° C. |

Figure 1:
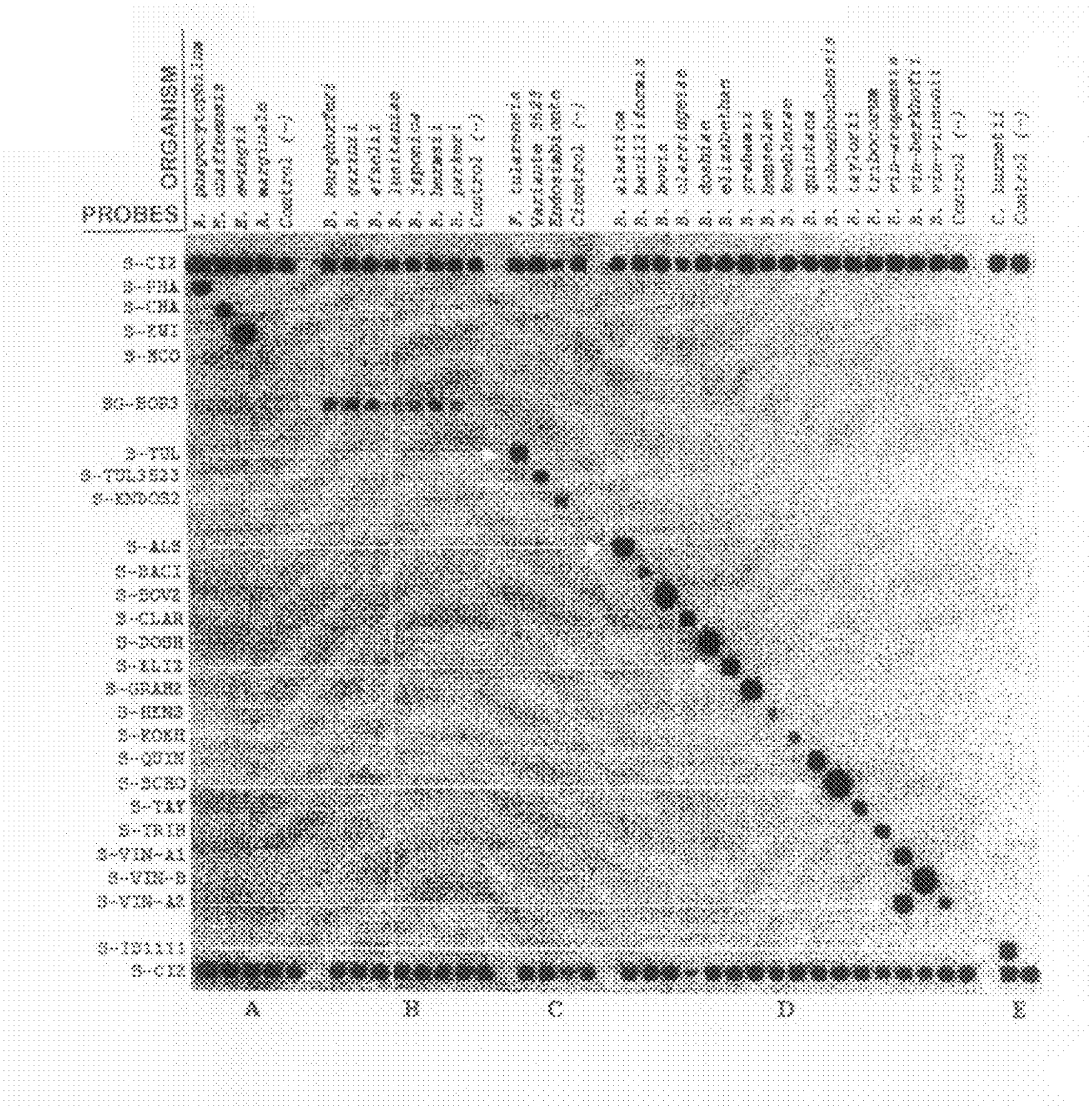

Hybridization results are shown in FIGS. 1 and 2A, where it is shown that each of the probes of the invention become joined specifically to the amplicons of each of the bacterial species detected using the method of the invention.

Preparation of Samples and Multiple PCR

One of the advantages of using PCR and RLB analysis-based identification systems is that pure bacterial cultures are not required. In this manner and upon validation of the primers and probes using DNA samples of the different species and subspecies listed in Tables 1-6, prepared following the procedures listed in Table 8 and analyzed in duplicate, a Multiple PCR-based analysis of a DNA control mixture prepared under laboratory conditions was carried out, followed by the RLB test, using the specifically designed primers and probes and the previously indicated temperature cycles and reaction mixture composition, the results of which are shown in FIG. 2B. In said figure it is shown that it was possible to carry out the simultaneous detection of the bacterial species present in the sample.

Detection of PCR Inhibitors

An internal amplification control (IAC), which was amplified together with the target DNA, was created for the detection of PCR inhibitors, using specific primers (Table 7) designed according to the conserved regions of the AB183705 sequence (Table 7) belonging to the THC synthase gene of the *Cannabis sativa* species. Specifically, the IAC amplicon corresponds to a sequence of 371 pairs of bases, for which a probe was also designed (Table 7) for detection during RLB analysis.

Specificity of the Method

The high specificity of this method is based on the specificity of the primers and their probes, which were tested with another series of organisms (Table 9), following the method described by the present invention, verifying that the formation of amplicons detectable by means of hybridization (FIG. 3) was not detected in any case.

TABLE 9

| Specificity: unrelated species of bacteria, arthropods and mammals used in method development | | | |
|---|---|---|---|
| | SPECIES | RLB RESULT | |
| All All | Bacteria | | All All |
| 1 | *Brucella melitensis* | Negative | |
| 2 | *Chlamydia pneumoniae* | Negative | |
| 3 | *C. psittaci* | Negative | |
| 4 | *Escherichia coli* | Negative | |
| 5 | *Legionella pneumophila* | Negative | |
| 6 | *Leptospira interrogans* | Negative | |
| 7 | *Mycoplasma pneumoniae* | Negative | |
| 8 | *Ochrobactrum antropi* | Negative | |
| 9 | *Orientia tsutsugamushi* | Negative | |
| 10 | *Pseudomonas aeruginosa* | Negative | |
| 11 | *Salmonella enterica* Typhi | Negative | |

TABLE 9-continued

| Specificity: unrelated species of bacteria, arthropods and mammals used in method development | | |
|---|---|---|
| | SPECIES | RLB RESULT |
| 12 | *Streptococcus pneumoniae* | Negative |
| 13 | *Treponema pallidum* | Negative |
| | Arthropods | Negative |
| 14 | *Ixodes ricinus* | Negative |
| 15 | *Dermacentor marginatus* | Negative |
| 16 | *Rhipicephalus sanguineus* | Negative |
| | Mammals | Negative |
| 17 | *Apodemus sylvaticus* | Negative |
| 18 | Human | Negative |

All references cited and/or discussed in this specification are incorporated herein by reference in their entireties and to the same extent as if each reference was individually incorporated by reference.

The invention claimed is:

1. A method for the simultaneous detection of bacterial species that cause zoonosis belonging to the genera *Anaplasma, Ehrlichia, Bartonella, Borrelia, Coxiella, Francisella* and *Rickettsia* comprising the following steps:

(a) placing a sample for analysis in contact with a reaction mixture containing specific primers SEQ ID NOs: 1, 2, 7, 8, 25, 26, 28, 29, 31, 32, 36 and 37, to perform multiplex polymerase chain reaction;

(b) amplifying the sequences by means of polymerase chain reaction: and (c) detecting and identifying the amplification products formed in the previous step, said detection information being indicative of the presence or absence of zoonosis-causing bacteria.

2. The method of claim 1, wherein the bacterial species are:

(a) *Anaplasma phagocytophilum, A. Bovis, A. equi, A. marginale, A. centrale* and *A. ovis;*

(b) *Ehrlichia chaffeensis* and *E. Ewingii;*

(c) *Bartonella henselae, B. quintana, B. clarridgeiae, B. elizabethae, B. grahamii, B. vinsonii* subspecies *berkhofii, B. vinsonii* subspecies *vinsonii, B. vinsonii* subspecies *aurupensis, B. bacilliformis, B. alsatica, B. bovis, B. doshiae, B. koehlerae, B. schoenbuchensis, B. taylori* and *B. tribocorum;*

(d) species belonging to the genus *Borrelia;*

(e) *Coxiella burnetti;*

(f) any subspecies of *Francisella turalensis*, including *F. tularensis* subsp. *tularensis, F. tularensis* subsp. *holartica* and *F. tularensis* subsp. *novicida* which are jointly detected, and variant 3523 of the same species and so-called endosymbionts of different species ixodides and argasides, which are differentially detected; and (g) species belonging to the genus *Rickettsia*, the group that causes spotted fever, and the group that causes typhus; and the species *Rickettsia akari, R. bellii, R. slovaca, R. conorii, R. aeschilmannii, R. ricketsii, R. sibirica, R. helvetica, R. felis, R. australis, R. prowazekii*, and *R. typhy* (r. *mooserii*).

3. The method of claim 1, wherein the simultaneous detection of the amplification products is carried out using one or more probes having a sequence selected from SEQ ID NOs: 3-6, 9-24, 27, 30, 33-35, and 38-51.

4. The method of claim 1, further comprising the use of at least one internal amplification control.

5. The method of claim 4, wherein the use of the internal amplification control comprises:

(a) amplifying SEQ ID NO: 94 with specific primers; and (b) detecting the amplification product formed in the previous step.

6. The method of claim 5, wherein one or more of the specific primers has a sequence selected from SEQ ID NOs: 52 and 53.

7. The method of claim 4, wherein the amplification product detection is carried out using the probe with SEQ ID NO: 54.

* * * * *

SEQUENCE LISTING

<160> NUMBER OF SEQ ID NOS: 94

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
cagaacgaac gctggcggca ag 22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gcattactca cccgtctgcc actc 24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic probe

<400> SEQUENCE: 3
ggmttattct ttatagcttg ct 22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
attgcttata accttttggt t 21

<210> SEQ ID NO 5
<211> LENGTH: 21
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 5

gaacaattcc taaatagtct c                                               21


<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6

cagcttgctg cgtgtatgg                                                  19


<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

ttgataagcg tgaggtcgga gg                                              22


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

caaagcaggt gctctcccag                                                 20


<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

atcggttcaa tcatatcgct tt                                              22


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10

cgcttatcca tttggtttaa                                                 20


<210> SEQ ID NO 11
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 11

acgatgctaa aagttgctat                                                20


<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12

taagttccct tcaagaggat a                                              21


<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13

attcaagttg atgaatttgg ttat                                           24


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14

tttcggacac tattgataaa                                                20


<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15

acttgttgga attgcttaac c                                              21


<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16

atgaaaatat tgagagattt g                                              21


<210> SEQ ID NO 17
<211> LENGTH: 20
<212> TYPE: DNA
<213> ORGANISM: Artificial Sequence
```

<220> FEATURE:
<223> OTHER INFORMATION: Description of Artificial Sequence: Synthetic
probe

<400> SEQUENCE: 17
cctatgattg atttctaggc 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 18
gctggtgaaa cttgcttata 20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 19
cgttttgata gtcttttgtg ttgc 24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 20
tttgaacctt ctctctttat 20

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
probe

<400> SEQUENCE: 21
ttaaattata tcactttggg tcatacg 27

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
probe

<400> SEQUENCE: 22
gctgataagt ttgctgataa g 21

<210> SEQ ID NO 23
<211> LENGTH: 19
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 23

tatccatttc gcttaggca                                                      19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24

ttctattaag tttgtcaaag gg                                                  22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

taagaatctt ccgcaatggg c                                                   21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

atccgcctac tcacccttta c                                                   21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

tgacggagcg acactgcgtg                                                     20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

tatgtatcca ccgtagccag tc                                                  22

<210> SEQ ID NO 29
<211> LENGTH: 21
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 29
cccaacaaca cctccttatt c 21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 30
gcaagaatac ggactcacga 20

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
gyaggtttag ckagctgttc tac 23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
ggagcytgcc attgtaatct tac 23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
probe

<400> SEQUENCE: 33
agatactgct gctgctcaga cag 23

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 34
gcatcagata agggcaccgc 20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
probe

<400> SEQUENCE: 35
cagctacacc aacrgccgta g 21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
gataggtcrg rtgtggaagc ac 22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
tcgggayggg atcgtgtgtt tc 22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
probe

<400> SEQUENCE: 38
tagctcgatt grtttacttt g 21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
probe

<400> SEQUENCE: 39
actcacaarg ttatcaggt 19

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
probe

<400> SEQUENCE: 40
gatcatgcag caatacatta gc 22

<210> SEQ ID NO 41
<211> LENGTH: 23
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 41

gtgtttattc tataatatgt cag                                             23


<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42

gtagcccctg ccacgata                                                   18


<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43

gttatatact gtagccctg                                                  19


<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44

atattatact gtatgtagcc cc                                              22


<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45

gttatactgt agtcctgcaa                                                 20


<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46

catggcttga tccacggta                                                  19


<210> SEQ ID NO 47
<211> LENGTH: 22
<212> TYPE: DNA
<213> ORGANISM: Artificial Sequence
```

<220> FEATURE:
<223> OTHER INFORMATION: Description of Artificial Sequence: Synthetic
probe

<400> SEQUENCE: 47
taatgttata ccgtggtccc gc 22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
probe

<400> SEQUENCE: 48
gacaagttta gttatgcaat 20

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 49
gttattctat cgttttatgt yacg 24

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
probe

<400> SEQUENCE: 50
tacgatttga tagtaaagtt ttg 23

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
probe

<400> SEQUENCE: 51
atgtcacgat ttgaccgtaa gatc 24

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
atgatgctga gggtatgtcc tac 23

<210> SEQ ID NO 53
<211> LENGTH: 21
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 53
gttttctcct ccaccaccac g 21

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gtggacactt tagtggagga gg 22

<210> SEQ ID NO 55
<211> LENGTH: 377
<212> TYPE: DNA
<213> ORGANISM: Rickettsia felis

<400> SEQUENCE: 55
gataggtcgg gtgtggaagc acagtaatgt gtgtagctaa ctgatactaa tagctcgatt 60
gatttacttt gctgtgagat tacatatgca tatagtgtta attctataaa aatgtagtat 120
caactcacaa agttatcagg ttaaattagc tttaccaatg aataaaaatg ttgttgcaca 180
gctaataatg ttataccgtg gtcccgccac ggtatctaga aaaattttta atatttagat 240
tcttgcttcc gcaggaatga taaatttagt catgcaacaa cattaacagc aaactataat 300
acaaatctat ctttttaaaa gtttgtattg ctagcttggt ggttatagca tgagtgaaac 360
acacgatccc atcccga 377

<210> SEQ ID NO 56
<211> LENGTH: 343
<212> TYPE: DNA
<213> ORGANISM: Rickettsia australis

<400> SEQUENCE: 56
ccgatactaa tagctcgatt gatttacttt gctgtgggat tacatatgca tatggtgtta 60
attctataaa catgtaagtg tcaactcaca aagttatcag gttaaattag ctttatcaat 120
gaataaagat gttgttgcac agctaataat gtcatctcgt ggcttgacca cagtatctag 180
cagtatctag aaaaatttat aatatttgga ttcctgcttc cgtaggagtg acaagtttag 240
ttatgcaata acattaacag cgaactataa tacaaatcta ttttttttaaa agtttgtatt 300 gctagcttgg tggttatagc atgagtgaaa cacacgatcc cga 343

<210> SEQ ID NO 57
<211> LENGTH: 22
<212> TYPE: DNA
<213> ORGANISM: Anaplasma phagocytophilum

<400> SEQUENCE: 57
agcaagctat aaagaataak cc 22

<210> SEQ ID NO 58
<211> LENGTH: 21
<212> TYPE: DNA
<213> ORGANISM: Ehrlichia chaffeensis

<400> SEQUENCE: 58
aaccaaaagg ttataagcaa t 21

<210> SEQ ID NO 59
<211> LENGTH: 21
<212> TYPE: DNA
<213> ORGANISM: Erlichia ewingii

<400> SEQUENCE: 59
gagactattt aggaattgtt c 21

<210> SEQ ID NO 60
<211> LENGTH: 19
<212> TYPE: DNA
<213> ORGANISM: Anaplasma marginale

<400> SEQUENCE: 60
ccatacacgc agcaagctg 19

<210> SEQ ID NO 61
<211> LENGTH: 22
<212> TYPE: DNA
<213> ORGANISM: Bartolella henselae

<400> SEQUENCE: 61
aaagcgatat gattgaaccg at 22

<210> SEQ ID NO 62
<211> LENGTH: 20
<212> TYPE: DNA
<213> ORGANISM: Bartonella quintana

<400> SEQUENCE: 62
ttaaaccaaa tggataagcg 20

<210> SEQ ID NO 63
<211> LENGTH: 20
<212> TYPE: DNA
<213> ORGANISM: Bartonella clarridgeiae

<400> SEQUENCE: 63
atagcaactt ttagcatcgt 20

<210> SEQ ID NO 64
<211> LENGTH: 21
<212> TYPE: DNA
<213> ORGANISM: Bartonella elizabethae

<400> SEQUENCE: 64
tatcctcttg aagggaactt a 21

<210> SEQ ID NO 65
<211> LENGTH: 24
<212> TYPE: DNA
<213> ORGANISM: Bartonella grahamii

<400> SEQUENCE: 65
ataaccaaat tcatcaactt gaat 24

<210> SEQ ID NO 66
<211> LENGTH: 20
<212> TYPE: DNA
<213> ORGANISM: Bartonella vinsonii berkhofii

<400> SEQUENCE: 66
tttatcaata gtgtccgaaa 20

<210> SEQ ID NO 67
<211> LENGTH: 21
<212> TYPE: DNA
<213> ORGANISM: Bartonella vinsonii arupensis

<400> SEQUENCE: 67
ggttaagcaa ttccaacaag t 21

<210> SEQ ID NO 68
<211> LENGTH: 21
<212> TYPE: DNA
<213> ORGANISM: Bartonella vinsonii vinsonii

<400> SEQUENCE: 68
caaatctctc aatattttca t 21

<210> SEQ ID NO 69
<211> LENGTH: 20
<212> TYPE: DNA
<213> ORGANISM: Bartonella bacilliformis

<400> SEQUENCE: 69
gcctagaaat caatcatagg 20

<210> SEQ ID NO 70
<211> LENGTH: 20
<212> TYPE: DNA
<213> ORGANISM: Bartonella alsatica

<400> SEQUENCE: 70
tataagcaag tttcaccagc 20

<210> SEQ ID NO 71
<211> LENGTH: 24
<212> TYPE: DNA
<213> ORGANISM: Bartonella bovis

<400> SEQUENCE: 71
gcaacacaaa agactatcaa aacg 24

<210> SEQ ID NO 72
<211> LENGTH: 20
<212> TYPE: DNA
<213> ORGANISM: Bartonella doshiae

<400> SEQUENCE: 72
ataaagagag aaggttcaaa 20

<210> SEQ ID NO 73
<211> LENGTH: 27
<212> TYPE: DNA
<213> ORGANISM: Bartonella koehlerae

<400> SEQUENCE: 73
cgtatgaccc aaagtgatat aatttaa 27

<210> SEQ ID NO 74
<211> LENGTH: 21
<212> TYPE: DNA
<213> ORGANISM: Bartonella schoenbuchensis

<400> SEQUENCE: 74
cttatcagca aacttatcag c 21

<210> SEQ ID NO 75
<211> LENGTH: 19
<212> TYPE: DNA
<213> ORGANISM: Bartonella taylori

<400> SEQUENCE: 75
tgcctaagcg aaatggata 19

<210> SEQ ID NO 76
<211> LENGTH: 22
<212> TYPE: DNA
<213> ORGANISM: Bartonella tribocorum

<400> SEQUENCE: 76
ccctttgaca aacttaatag aa 22

<210> SEQ ID NO 77
<211> LENGTH: 20
<212> TYPE: DNA
<213> ORGANISM: Borrelia burgdorferi sensu lato

<400> SEQUENCE: 77
cacgcagtgt cgctccgtca 20

<210> SEQ ID NO 78
<211> LENGTH: 20
<212> TYPE: DNA
<213> ORGANISM: Coxiella burnetii

<400> SEQUENCE: 78
tcgtgagtcc gtattcttgc 20

<210> SEQ ID NO 79
<211> LENGTH: 23
<212> TYPE: DNA
<213> ORGANISM: Fracisiella tularensis

<400> SEQUENCE: 79
ctgtctgagc agcagcagta tct 23

<210> SEQ ID NO 80
<211> LENGTH: 20
<212> TYPE: DNA
<213> ORGANISM: Fraciliella turalensis

<400> SEQUENCE: 80
gcggtgccct tatctgatgc 20

<210> SEQ ID NO 81
<211> LENGTH: 21
<212> TYPE: DNA
<213> ORGANISM: Francisiella endosimbionte

<400> SEQUENCE: 81
ctacggcygt tggtgtagct g 21

<210> SEQ ID NO 82
<211> LENGTH: 21
<212> TYPE: DNA
<213> ORGANISM: Rickettsia conorii -continued

<400> SEQUENCE: 82
caaagtaaay caatcgagct a 21

<210> SEQ ID NO 83
<211> LENGTH: 19
<212> TYPE: DNA
<213> ORGANISM: Rickettsia conorii

<400> SEQUENCE: 83
acctgataac yttgtgagt 19

<210> SEQ ID NO 84
<211> LENGTH: 22
<212> TYPE: DNA
<213> ORGANISM: Rickettsia akari

<400> SEQUENCE: 84
gctaatgtat tgctgcatga tc 22

<210> SEQ ID NO 85
<211> LENGTH: 23
<212> TYPE: DNA
<213> ORGANISM: Rickettsia bellii

<400> SEQUENCE: 85
ctgacatatt atagaataaa cac 23

<210> SEQ ID NO 86
<211> LENGTH: 18
<212> TYPE: DNA
<213> ORGANISM: Rickettsia slovaca

<400> SEQUENCE: 86
tatcgtggca ggggctac 18

<210> SEQ ID NO 87
<211> LENGTH: 19
<212> TYPE: DNA
<213> ORGANISM: Rickettsia conorii

<400> SEQUENCE: 87
cagggctaca gtatataac 19

<210> SEQ ID NO 88
<211> LENGTH: 22
<212> TYPE: DNA
<213> ORGANISM: Rickettsia aeschlimannii

<400> SEQUENCE: 88
ggggctacat acagtataat at 22

<210> SEQ ID NO 89
<211> LENGTH: 20
<212> TYPE: DNA
<213> ORGANISM: Rickettsia rickettsii

<400> SEQUENCE: 89
ttgcaggact acagtataac 20

<210> SEQ ID NO 90
<211> LENGTH: 19
<212> TYPE: DNA
<213> ORGANISM: Rickettsia helvetica -continued

```
<400> SEQUENCE: 90

taccgtggat caagccatg                                                    19


<210> SEQ ID NO 91
<211> LENGTH: 24
<212> TYPE: DNA
<213> ORGANISM: Rickettsia prowazekii

<400> SEQUENCE: 91

cgtracataa aacgatagaa taac                                              24


<210> SEQ ID NO 92
<211> LENGTH: 23
<212> TYPE: DNA
<213> ORGANISM: Rickettsia prowazekii

<400> SEQUENCE: 92

caaaacttta ctatcaaatc gta                                               23


<210> SEQ ID NO 93
<211> LENGTH: 24
<212> TYPE: DNA
<213> ORGANISM: Rickettsia typhi

<400> SEQUENCE: 93

gatcttacgg tcaaatcgtg acat                                              24


<210> SEQ ID NO 94
<211> LENGTH: 22
<212> TYPE: DNA
<213> ORGANISM: Cannabis sativa

<400> SEQUENCE: 94

cctcctccac taaagtgtcc ac                                                22
```